(12) United States Patent
Forsythe et al.

(10) Patent No.: US 6,958,167 B2
(45) Date of Patent: Oct. 25, 2005

(54) METHOD FOR APPLYING AN AIR SUSPENSION OF MINUTE SOLID PARTICLES OF CIPC

(76) Inventors: Darol Forsythe, 15401 Cartwright Rd., Boise, ID (US) 83703; Craig Horn, 6617 W. Summerhill, Boise, ID (US) 83703

( * ) Notice: Subject to any disclaimer, the term of this patent is extended or adjusted under 35 U.S.C. 154(b) by 190 days.

(21) Appl. No.: 10/094,109

(22) Filed: Mar. 8, 2002

(65) Prior Publication Data

US 2002/0136839 A1 Sep. 26, 2002

Related U.S. Application Data

(60) Provisional application No. 60/274,370, filed on Mar. 8, 2001.

(51) Int. Cl.$^7$ .............................. A23B 7/00; A23L 3/34
(52) U.S. Cl. ...................... 426/321; 426/335; 426/615; 426/637
(58) Field of Search ................................ 426/294, 320, 426/321, 335, 615, 637

(56) References Cited

U.S. PATENT DOCUMENTS

| | | |
|---|---|---|
| 2,341,868 A | 9/1944 | Hitchcock et al. |
| 3,128,170 A | 4/1964 | Plant |
| 3,857,511 A | 12/1974 | Govindan |
| 4,226,179 A | 10/1980 | Sheldon, III et al. |
| 4,887,525 A | 12/1989 | Morgan |
| 5,622,912 A | 4/1997 | Riggle et al. |
| 5,723,184 A | 3/1998 | Yamamoto |
| 5,935,660 A * | 8/1999 | Forsythe et al. ............ 427/446 |
| 5,965,489 A | 10/1999 | Forsythe et al. |
| 6,068,888 A * | 5/2000 | Forsythe et al. ............ 427/446 |
| 6,432,882 B1 | 8/2002 | Yamamoto |
| 6,790,469 B2 * | 9/2004 | Robbs et al. ............... 426/335 |

FOREIGN PATENT DOCUMENTS

| | | |
|---|---|---|
| CA | 1 203 394 | 4/1986 |

OTHER PUBLICATIONS

Dennis, Frank G. "Dormancy: Manifestations and Causes" Chapter 20 in Handbook of Plant and Crop Physiology, Mohammad Pessarakli ed. NY: Marcel Dekker, Inc. pp. 437–450, 1995.

Shetty, et al., Fine–Tuning Time for Inhibition Potato Grower of Idaho, Dec. 1993, pp. 14–15, 1993.

* cited by examiner

*Primary Examiner*—Leslie Wong
(74) *Attorney, Agent, or Firm*—TraskBritt

(57) ABSTRACT

A method for applying an air suspension of minute solid particles of CIPC to a potato storage facility at ambient temperatures. The minute solid particles are produced from larger solid particles of solid CIPC by micronizing the larger particles.

12 Claims, 1 Drawing Sheet

# METHOD FOR APPLYING AN AIR SUSPENSION OF MINUTE SOLID PARTICLES OF CIPC

CROSS-REFERENCE TO RELATED APPLICATION

Pursuant to the provisions of 35 U.S.C. 119(e), this application claims the benefit of the filing date of provisional patent application Ser. No. 60/274,370, filed Mar. 8, 2001, for "Method For Applying an Air Suspension of Minute Solid Particles of CIPC."

BACKGROUND OF THE INVENTION

1. Field of the Invention

The invention relates generally to methods and techniques for applying sprout inhibitors to potato storage facilities.

2. State of the Art

Potatoes are stored frequently over the off-season at cool temperatures in large storage facilities. A commercial sprout inhibitor has been chemically identified as Chloroisopropyl-N-carbonate (CIPC). To prevent sprouting of the potatoes, it has been conventional to treat them during storage with an aerosol of CIPC, typically derived from a solution of CIPC via a thermal aerosol device. More recently, as exemplified by U.S. Pat. Nos. 5,935,660 and 5,965,489 to Forsythe et al., the aerosol has been derived from molten CIPC.

The technique described in these two patents is in use currently as the preferred commercial method of applying CIPC to potato storage facilities.

Using an aerosol derived from solid CIPC eliminates the introduction of solvent into the storage facility, which has certain advantages. The use of thermal aerosol generators introduces a heated aerosol stream of CIPC droplets, which cool into minute solid particles before or after contacting stored potatoes. The introduction of a warm stream into the potato storage facility may raise the temperature of the facility, which, under some conditions, tends to induce sprouting. Techniques of applying CIPC at cold temperatures have not generally been commercially economic or have been technically unsuccessful. The technique of the Plant patent U.S. Pat. No. 3,128,170 creates an aerosol of a solvent-CIPC system without use of a thermal generator, however, it was supplanted by thermal aerosol generators using a CIPC-solvent solution prior to the developments described in the above-identified Forsythe patents.

BRIEF DESCRIPTION OF THE SEVERAL VIEW OF THE DRAWINGS

DETAILED DESCRIPTION OF THE INVENTION

A method for applying an air suspension of micron-sized particles of CIPC derived directly from larger, solid CIPC particles has been invented. The larger particles of CIPC, which may be flakes, shavings, pellets or chunks of solid CIPC, are directed into a micronizing device, such as that illustrated in FIG. 1. A cloud of micron-sized particles is formed in the micronizing device. This cloud is conveyed to a potato storage facility.

The micron-sized particles are preferably less than 10 microns in size and, more desirably, less than about 5 microns. Particles larger than 10 microns do not tend to stay in suspension. The micronizing devices may produce particles of a wide variety of sizes so that a separation step is used to collect larger particles which drop from the "cloud" of smaller, suspended particles. Separation of ultra-fine, e.g., less than one micron may also be desirable.

Figure 1:
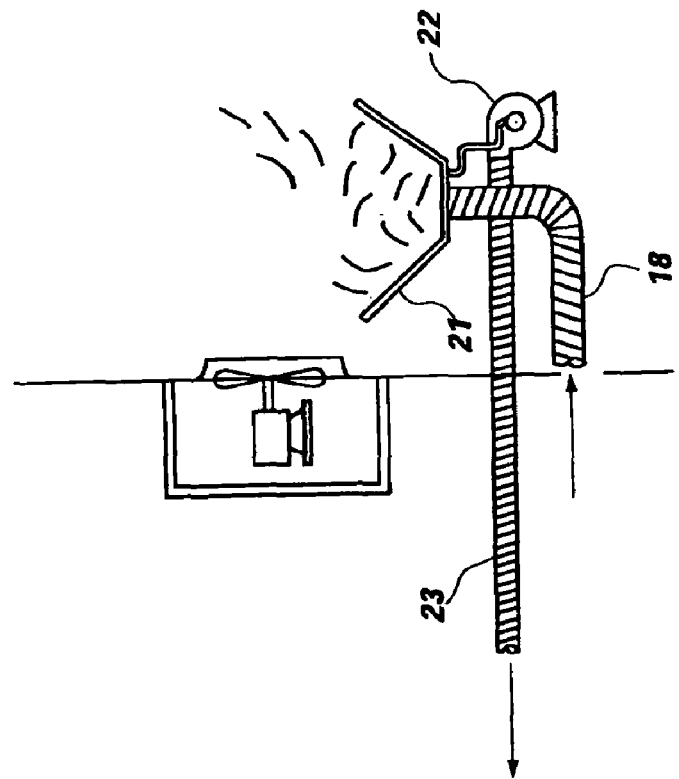
FIG. 1 is a cross-sectional view of a micronizing device.
Figure 2:
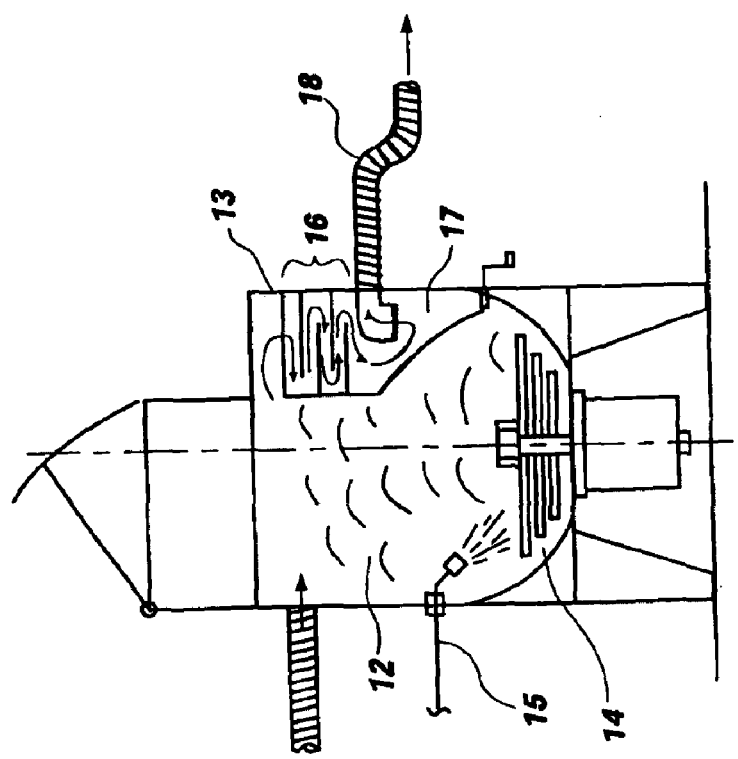
FIG. 2 is a cross-sectional schematic showing the storage fan and blower.

Further understandings of the invention may be facilitated by reference to FIGS. 1 and 2.

A micronizing device 13 is shown with a feed chute for solid CIPC flakes, briquettes, pellets and the like which direct them into contact with high speed revolving blades 14 to produce a cloud of minute solid particles of CIPC. The solid CIPC feed material is preferably at a temperature significantly less than its melting point. In a preferred technique, the solid CIPC feed material as cooled to a temperature sufficiently low that the micronizing step does not heat the surface of any CIPC micronizing particles to or above the melting point of CIPC.

A stream of compressed air 15 is preferably directed toward the revolving blades to cool them and the minute particles produced by the blades. CIPC solid material has a melting point of about 105° F. The fragmentation of the larger CIPC particles, e.g., flakes, into minute particles, especially micron-sized particles, may be accompanied by a rise in temperature by the friction between blades and solids. Such an increase in temperatures may be sufficient to cause some melting at the surface of the minute particles. Any melting at the surface of particles may cause agglomeration of the finer particles. Agglomeration of fine particles may tend to minimize the number of particles sufficiently small to remain suspended in an air stream for a sufficient period of time to be circulated about and through a large pile of potatoes to achieve uniform distribution of minute CIPC particles through a large pile of stored potatoes.

Thus, introduction of compressed air into the micronizing device provides air to suspend the fine particles and tends to cool the micronizing step as the air expands from a high pressure to a low pressure region within the chamber of the micronizing devices. If a large volume of air is introduced, it may be at ambient temperatures since a less dense cloud of particles would have less collision of "tacky" particles. In such a case, a large blower may be substituted for the air compressor.

The cloud of minute particles is directed through a separation chamber 17 provided with baffles 16 to cause directional change of the suspended particles (cloud) and allow the larger particles to drop out before the cloud of remaining fine particles is introduced into duct 18 for conveyance to a potato storage facility.

Potato storage facilities are typically maintained at temperatures less than 55° F. and preferably between about 42° to 50° F. While thermal aerosol generators create aerosols at about 500° F. and higher, the instant invention is capable of providing a stable suspension of micron-sized particles at low temperatures, particularly below 100° F. and even at lower temperatures, e.g., 40–50° F., thus, not affecting adversely the temperature of the storage facility.

In FIG. 2, the cloud of suspended minute particles, typically less than 10 microns, is conducted through duct 18 to a distributor 21 having a cone such that larger particles which drop out upon the release from the duct and collected so that such fallen particles are blown by blower 22 through return duct 23 to the micronizer.

The creation of a cloud of minute CIPC particles was accomplished by feeding small chunks of solid CIPC into a high-speed, coffee-bean-grinder type machine. The cloud of CIPC particles created stayed in suspension for a significant period of time.

This cloud of particles was suitable for conveyance to stored potatoes and suitable for effective distribution of CIPC particles onto such a pile of potatoes.

Various types of micronizing devices may be utilized to produce micron-sized particles, preferably of a size less than about 10 microns.

Although CIPC is a waxy type of crystalline material, it is effectively micronized in a high speed bladed device. Typical blade speeds may be about 1,200 rpm to 10,000 rpm. Rotational speeds of about 3,500 rpm produce a suitable cloud of CIPC particles.

Separation of larger particles, e.g., greater than 10 microns, is desirable since such larger particles will not stay suspended and will deposit upon the conveyance duct work and the air circulation ducts in a storage facility. Also, return of such oversized particles to the micronizing device improves the efficient use of material. Cyclone separators and other solid separators may be effectively used to remove oversized particles. Such separation devices are preferably positioned closely adjacent to or as an integral part of the micronizer.

Although large chunks or briquettes of solid CIPC may be effectively micronized, presizing of the solid CIPC to be fed to the micronizer may be generally desirable. Thus, solid flakes or pea sized or BB sized CIPC solid particles which can readily be produced by a CIPC manufacturer are preferred to improve the efficiency of the micronizer and produce micron-sized particles of the proper size range.

Generally, particles less than one micron are not desirable since these may stay suspended for too long a period thus not permitting entry to a storage facility for too many days for maintenance, inspection, etc. Sizing separators may be utilized to remove both the oversized and undersized particles. Undersized particles may collect and then be heated above the melting point of CIPC to agglomerate them for return to the micronizer.

Proper sizing of the feed CIPC solid particles and adjustment of the rotational speed of the micronizing blades and selection of the proper number and size of the blades will produce a cloud of micron-sized particles with a desirable size distribution.

Chilling of the feed solid CIPC particles may be desirable to cause the waxy CIPC to be more frangible and reduce agglomeration in maintaining surface temperatures well below the melting point of CIPC. Also, the compressed air injected into the micronizer may be chilled to reduce agglomeration and build-up of CIPC in the micronizer blades and apparatus surface.

Other types of micronizers such as hammer mills and the like may be used to produce a cloud of micron-sized CIPC particles. Micronizers of the type used to produce inhalable clouds of solid medications may be used in the instant invention.

Various techniques may be utilized to maintain the micronized particles in a sufficiently cooled state to minimize agglomeration. Besides chilling the carrier air and/or the solid CIPC full, a solid mixture of CIPC and water (ice) may be used as CIPC feed material to a micronizer. For example, minute particles of CIPC may be formed as a water slurry and frozen before the CIPC particles settle. Such a CIPC/ice solid mixture is fed to the micronizer preferably at temperatures less than 32° F. A cloud of micron-sized CIPC and ice may then be formed for distribution to a potato storage facility. The temperature of the storage facility is typically above about 42° F., so the ice will melt into very small micron-sized water droplets which will generally stay suspended a sufficiently long time that the relatively high vapor pressure of the water will cause said micron-sized droplets to evaporate and thus humidify the storage facility at the same time as the potatoes are being treated to prevent sprouting.

Mixtures of CIPC with other solids, e.g., other types of solid sprout inhibitors or herbicides, fungicides, etc. may be successfully applied by the technique of the instant invention.

For example, some alkylated naphthalene compounds, such as diisopropyl naphthalene, which is solid at room temperature, have been suggested and tested as potato sprout inhibitors. Such solid chemicals could simultaneously or sequentially be formed into micron-sized particles in a stable air suspension for treatment of a potato storage facility. Such solid chemicals could, of course, be formed into pellets, flakes and the like in combination with CIPC.

Also, gaseous chemicals may be injected into the air streams prior to or after micronization. For example, it may be desirable to add a chemical in conjunction with CIPC which is gaseous at the micronizer or storage facility temperatures.

For example, it may be desirable to add a chemical in conjunction with CIPC which is gaseous at the micronizer or storage facility temperatures.

Application of dimethylnaphthalene (DMN), a liquid at room temperature, may have air bubbled through a container of DMN or have DMN atomized into the air stream prior to the micronizer or into the CIPC cloud following the micronizer.

DMN has been shown to possess dormancy enhancing characteristics for potatoes as well as promoting suberization. Thus, ceratin advantage may accrue through the concurrent or sequential application of DMN and CIPC micronized particles.

Alternatively, water or chemical such as DMN, which has a freezing point of about 17° F., can be frozen and introduced as ice particles in the air stream, as a separate stream or with the CIPC pellets, flakes or chunks. The introduction of such frozen particles into the micronizer will tend to maintain the micronizing elements whether they be blades, hammers, or similar fragmenting elements at a sufficiently cool temperature that CIPC does not accumulate on said fragmenting elements or on other surfaces of the micronizing device.

The instant invention includes the formation of micron-sized particles of CIPC at one site, for example, by grinding, comminuting or the like, sizing to obtain the proper sized particles, then shipping said particles in bulk to a storage facility for formation into an air suspension by introducing the particles into a stream of air of the proper velocity and volume to form a stable air suspension. Such air stream could be the air circulation stream of a storage facility.

The invention also includes formation of pellets, flakes or briquettes during the final processing steps of a CIPC manufacturing process. Such final steps may include prilling, extruding or like techniques of molten CIPC or evaporation of the solvent foam solution of CIPC to produce pellets, flakes or the like of an appropriate size for feeding to a micronizing device.

Also, the final processing steps of a CIPC manufacturing process may include steps such as those used to form silica gel and similar particles containing similar surface area per volume and low density which may be readily aerated to form stable air suspensions.

The technique of this invention may be applied to solids other than CIPC, such as chemicals which are solid at room temperature.

What is claimed is:

1. A method of providing a cold aerosol of substantially pure solid particles of CIPC for treatment of a vegetable storage facility comprising:

micronizing solid CIPC at a temperature below about 105° F. in a micronizer to form a cloud of cold micronized solid particles of CIPC;

directing an air stream into said cloud of micronized solid particles of CIPC, said air stream having a temperature less than the melting point of said CIPC to form an expanded cloud of solid particles of CIPC maintained at a temperature of less than about 105° F.;

separating larger solid particles of CIPC from smaller particles of CIPC in said expanded cloud of CIPC while maintaining temperatures of solid particles of CIPC less than the melting point of CIPC to form a stable aerosol of said smaller particles of CIPC; and directing said aerosol to the internal space of a vegetable storage facility to deposit small solid CIPC particles upon the contents of said facility.

2. The method of claim 1, wherein said aerosol of solid particles of CIPC is introduced into the air circulation system of said vegetable storage facility.

3. The method of claim 1, wherein a second step of separating larger solid particles of CIPC from said aerosol is utilized before said aerosol is introduced to said storage facility.

4. The method of claim 1, wherein said air stream is compressed air.

5. The method of claim 1, wherein the larger particles from said first separation step are returned to said micronizer.

6. The method of claim 1, wherein said first separation step separates particles greater than 10 microns from said smaller particles.

7. A method for comminution of larger particles of solid CIPC to micron-sized particles of CIPC comprising:

feeding particles of solid CIPC into a micronizing device having rapidly moving fragmentation elements;

feeding frozen particles of another chemical into said micronizing device wherein said frozen particles have a melting point significantly below the melting point of CIPC to maintain the interior surfaces of said micronizing device at temperatures less than melting point of CIPC introducing a carrier gas stream into said micronizing device.

8. The method of claim 7, wherein said frozen particles are introduced into said micronizing device to contact said fragmentation elements.

9. The method of claim 7, wherein said frozen chemical particles comprise a chemical which has a beneficial effect upon stored potatoes in the potato storage facility.

10. The method of claim 7, wherein said frozen chemical particles comprises ice (frozen water).

11. The method of claim 7, wherein said frozen chemical particles comprise DMN.

12. A method for micronizing larger particles of CIPC in a micronizing device having fragmentation elements to form micron-sized particles of CIPC comprising:

feeding a slurry of CIPC particles in a liquid carrier (including water) into the fragmentation elements of said micronizing devices, said CIPC being substantially insoluble in said liquid carrier and maintaining the temperature within said micronized device below about 105° F.;

feeding a carrier air stream into said micronizing device in sufficient volume to carry minute liquid droplets of said liquid carrier and micron-sized particles of CIPC as a stable suspension from said micronizing devices for application to stored potatoes.

* * * * *